(12) United States Patent
Giovanni et al.

(10) Patent No.: US 8,845,982 B2
(45) Date of Patent: Sep. 30, 2014

(54) TWO-STEP COLD FORMALIN FIXATION OF ORGANIC TISSUE SAMPLES

(75) Inventors: Bussolati Giovanni, Turin (IT); Visinoni Francesco, Mozzo (IT)

(73) Assignee: Milestone S.r.l., Sorisole (BG) (IT)

( * ) Notice: Subject to any disclaimer, the term of this patent is extended or adjusted under 35 U.S.C. 154(b) by 235 days.

(21) Appl. No.: 13/302,752

(22) Filed: Nov. 22, 2011

(65) Prior Publication Data
US 2012/0129169 A1 May 24, 2012

(30) Foreign Application Priority Data

Nov. 24, 2010 (EP) .................................. 10 425 360
Dec. 14, 2010 (EP) .................................. 10 194 999

(51) Int. Cl.
*A61B 10/00* (2006.01)
*G01N 1/30* (2006.01)
*G01N 1/31* (2006.01)

(52) U.S. Cl.
CPC ... *G01N 1/30* (2013.01); *G01N 1/31* (2013.01)
USPC .................. 422/536; 422/64; 422/65; 422/66; 422/67; 436/180

(58) Field of Classification Search
USPC ............................... 422/536, 63–67; 436/180
See application file for complete search history.

(56) References Cited

U.S. PATENT DOCUMENTS

| | | | |
|---|---|---|---|
| 6,087,134 A | 7/2000 | Saunders | |
| 2002/0177183 A1* | 11/2002 | Giberson et al. | ............. 435/40.5 |
| 2004/0043383 A1 | 3/2004 | Maria Van Dongen et al. | |

FOREIGN PATENT DOCUMENTS

| | | |
|---|---|---|
| EP | 1455174 A1 | 5/2003 |
| WO | WO2006/017942 A1 | 2/2006 |
| WO | WO2008081451 A3 | 10/2008 |

OTHER PUBLICATIONS

Blum, "Formaldehyde als Hartungsmittel," Z wiss Mikr. 1893;10:314 (with English translation), 4 pages.
Abramovitz et al., "Optimization of RNA extraction from FFPE tissues for expression profiling in the DASL assay," Biotechniques, Mar. 2008, vol. 44, pp. 417-423.
Burka, "RNase Activity in Erythroid Cell Lysates," The Journal of Clinical Investigation, vol. 48, 1969, pp. 1724-1732.
Chen et al., "Optimization of RNA extraction from formalin-fixed, paraffin-embedded lymphoid tissues," Diagn Mol Pathol, Jun. 2007, vol. 16, No. 2, pp. 61-72.
Chung et al., "Factors in Tissue Handling and Processing That Impact RNA Obtained From Formalin-fixed, Paraffin embedded Tissue," Journal of Histochemistry & Cytochemistry, vol. 56(11), 2008, pp. 1033-1042.
Dabbs, "Immunohistochemical Protocols," American Society for Clinical Pathology, 2008, vol. 129, pp. 355-356.
Ding et al., "Effect of formalin on extraction of mRNA from a formalin-fixed sample: a basic investigation," Scandinavian journal of clinical and laboratory investigation, 2004, vol. 64, pp. 229-235.

(Continued)

*Primary Examiner* — Jyoti Nagpaul
(74) *Attorney, Agent, or Firm* — Lee & Hayes, PLLC

(57) ABSTRACT

A method for fixation of organic tissue samples includes immersing a tissue sample in a solution of Formalin at a temperature of between 2° C. and 10° C. for a first time period (A), and immersing the tissue sample in a cold fixation dehydrating agent for a second time period (B) following the first time period. An automated tissue fixation system for fixating organic tissue samples in Formalin is also described.

6 Claims, 3 Drawing Sheets

(56) References Cited

OTHER PUBLICATIONS

Dotti et al., "Effects of formalin, methacarn, and fineFIX fixatives on RNA preservation," Diagn Mol Pathol, vol. 19, No. 2, Jun. 2010, pp. 112-122.

EP Search Report for EP Application No. EP 10 19 4999, mailed on Jan. 24, 2012, 6 pages.

Fox et al., "Formaldehyde fixation," Journal of Histochemistry & Cytochemistry, Aug. 1, 1985, retrieved from <<http://jhc.sagepub.com/content/33/8/845.citation>>, vol. 33, No. 8 pp. 845-853.

Goldstein et al., "Minimun Formalin Fixation Time for Consistent Estrogen Receptor Immunohistochemical Staining of Invasive Breast Carcinoma," American Journal of Clinical Pathology, 2003, vol. 120, pp. 86-92.

Goldstein et al., "Recommendations for improved standardization of immunohistochmistry," Appl Immunohistochem Mol Morphol. Jun. 2007, vol. 15, No. 2, pp. 124-133.

Helander, "Kinetic studies of formaldehyde binding in tissue," Biotech Histochem, 1994, Williams & Wilkins, Volue 69, No. 3, pp. 177-179.

Hewitt et al., "Tissue handling and specimen preparation in surgical pathology: issues concerning the recovery of nucleic acids from formalin-fixed, parafin-embedded tissue," Archives of pathology & laboratory medicine. Dec. 2008, vol. 132, pp. 1929-1935.

Jones, "The reaction of formaldehyde with unsaturated fatty acids during histological fixation," The Histochemical journal. Nov. 27, 1969, pp. 459-491.

Lewis et al., "Unlocking the archive—gene expression in paraffin-embedded tissue," The Journal of pathology. copyright 2001, John Wiley & Sons, Ltd. 195, pp. 66-71.

Masuda et al., "Analysis of chemical modification of RNA from formalin-fixed samples and optimization of molecular biology applications for such samples," Oxford University Press, Nucleic Acids Research, 1999, vol. 27, No. 22, pp. 4436-4443.

Medeiros et al., "Tissue Handling for Genome-Wide Expression Analysis: A Review of the Issues, Evidence, and Opportunities," Archives of Pathology & Laboratory Medicine. Dec. 2007, vol. 131, pp. 1805-1816.

Paska et al., "Effect of formalin, acetone, and RNAlater fixatives on tissue preservation and different size amplicons by real-time PCR from paraffin-embedded tissue," Diagn Mol Pathol, Dec. 2004, vol. 13, No. 4, pp. 234-240.

Pearse, "Histochemistry, theoretical and applied," Edinburgh, London and New York, 1980, Chapter 5, 6 pages.

Scicchitano et al., "Preliminary Comparison of Quantity, Quality, and Microarray Performance of RNA Extracted From Formalin-fixed, Paraffin-embedded, and Unifixed Frozen Tissue Samples," retrieved at <<http://jhc.sagepub.com/content/54/11/1229>>, Journal of Histochemistry & Cytochemistry, 2006, vol. 54, pp. 1229-1237.

Sompuram et al., "A Molecular Model of Antigen Retrieval Using a Peptide Array," American Society for Clinical Pathology, 2006, vol. 125, pp. 91-98.

Stanta et al., "RNA extracted from paraffin-embedded human tissues is amenable to analysis by PCR amplification," 304 BioTechniques, 1991, vol. 11: No. 3, 3 pages.

van Maldegem et al., "Effects of processing delay, formalin fixation, and immunohistochemistry on RNA Recovery From Formalin-fixed Paraffin-embedded Tissue Sections," Diagn Mol Pathol. Mar. 2008, vol. 17, No. 1, pp. 51-58.

Wolff et al., "American Society of Clinical Oncology/College of American Pathologists guideline recommendations for human epidermal growth factor receptor 2 testing in breast cancer," J Clin Oncol. 2007;25:118-145, Jan. 1, 2007, 28 pages.

\* cited by examiner

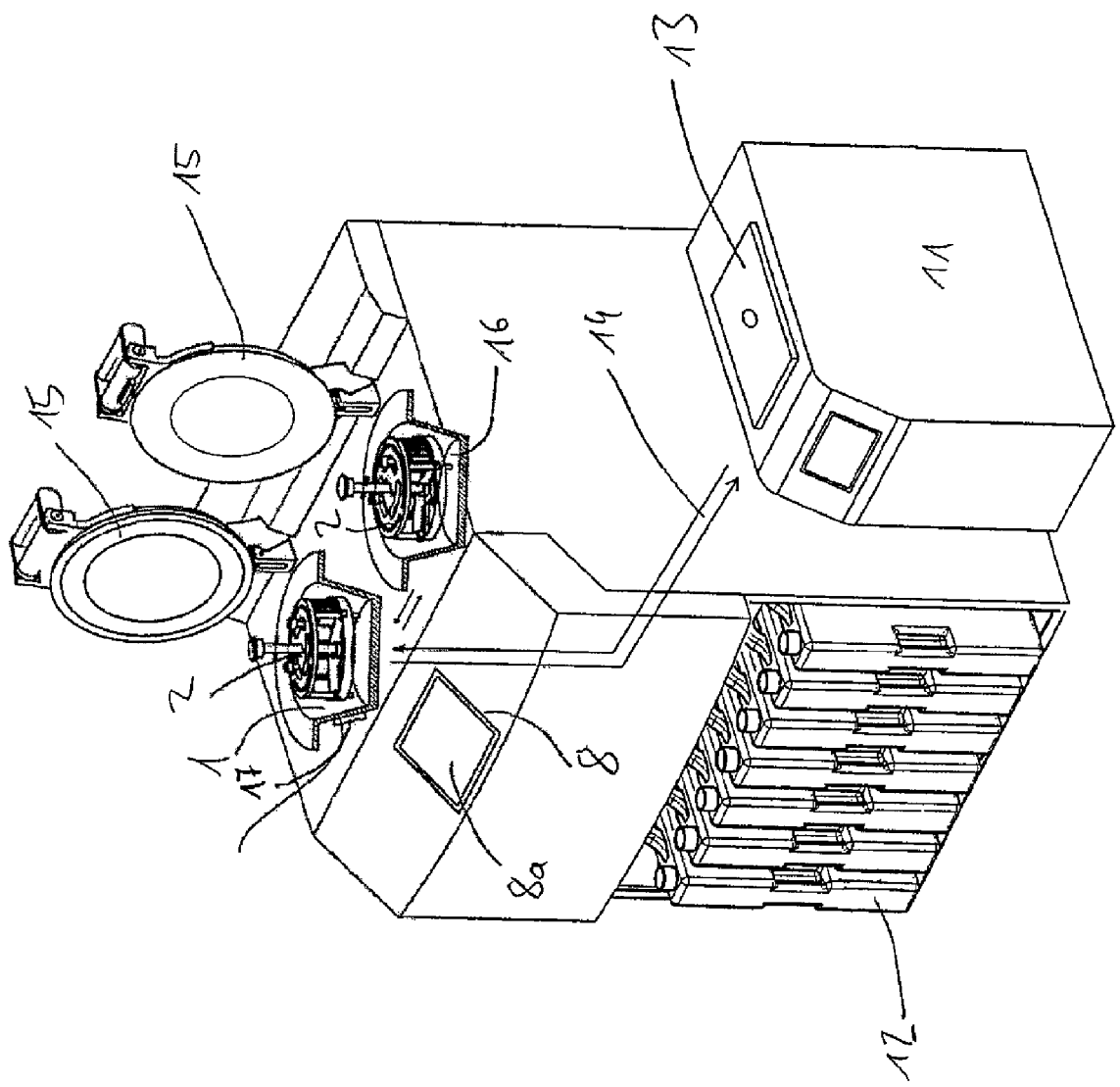

TWO-STEP COLD FORMALIN FIXATION OF ORGANIC TISSUE SAMPLES

This Application claims foreign priority to European Patent Application No. 10 425 360.4, filed Nov. 24, 2010, and European Patent Application No. 10 194 999.8, filed Dec. 14, 2010, both of which are incorporated herein by reference.

The present invention generally relates to the field of fixating organic tissue samples, typically for histopathology, using formalin.

STATE OF THE ART

A formaldehyde solution in water ("formalin") has been adopted as the fixative of choice in histopathology. A typical concentration thereby is between 3% and 8%. Fixation, a necessary process in the management of biopsies for histopathological diagnosis, allows preservation of tissue structure, cellular features and antigenic properties.

In recent times, requests for nucleic acid sequencing from formalin-fixed paraffin-embedded (FFPE) tissues has been stressing and extensive, since exploitation of the huge tissue archives would thus be opened to gene expression profile evaluation, with the goal of generating new and reliable diagnostic and prognostic parameters, especially on cancer (Madeiros et al., 2007; Lewis et al., 2001). Numerous studies have been conducted on the preservation status of nucleic acids in FFPE tissues, but a general agreement has been established on the fact that RNA was found to be heavily degraded and fragmented, so that only rather short sequences (in the order of 100-200 nucleotides) can be recognized and amplified (Chung et. al., 2006; Dotti, 2010; van Maldeghem, 2008; Paska, 2004; Masuda). The reasons of this effect are presently unknown.

The possibility of obtaining high quality mRNA from archival tissues might open prospects for gene expression profile analysis wider that those presently feasible (Scicchitano et al., 2006; Abramovitz et al., 2008) and to predict the clinical behaviour and therapeutic responsiveness of single malignant tumors, thus making tailored therapies feasible. At present, this approach requires collection of frozen samples, a procedure cumbersome and not always possible. The possibility of employing FFPE tissues for gene expression profiling would make extensive use of this molecular approach possible and easy even on archival tissues stored for long time in paraffin.

STATE OF THE ART

It is known to fix tissues (biopsies and surgical specimens for histopathological diagnosis) in 4% Formaldehyde in water of phosphate buffer 0.1 M PH 7.2 (Formalin). The number of specimens so processed is in the order of several millions worldwide. This fixation is commonly made by immersing tissue specimens in formalin for a time ranging from a few hours up to 24 hours. This is commonly done at room temperature. So far no reports have been made on the use of a treatment in cold formalin, in order to obtain at the same time histological preservation (for diagnosis) and preservation of RNA for molecular biological analysis and gene expression profiling.

OBJECT OF THE INVENTION

Requests for gene expression profiling for defining prognostic and therapeutic prospects in pathological lesions from single patients are pressing, since prospects are very promising, especially in breast, lung and colon cancer. At present, the only feasible approach is by collecting frozen samples (tissue banks) and to store this material, to be processed for gene expression analysis. The use of FFPE tissues would open great prospects and the exploitation of the huge archives present worldwide (see Chen et al, 2007; Scicchitano et al., 2006; Abramovitz et al., 2008).

It is therefore the object of the invention to propose an approach for improving the genetic integrity of Formalin fixed organic tissue samples.

This object is achieved by means of the features of the independent claims. The dependent claims develop further the central idea of the invention.

Note that in the framework of the present description and claims, "Formalin" simply is the short version for a diluted protein-crosslinking fixing agent. Thus, in this framework, "Formalin" is not limited to a formaldehyde solution in water.

In a first aspect, the present invention relates to method for fixation of organic tissue samples, the method comprising at least the steps of:

a.) immersing the tissue in a solution of Formalin at a temperature of between 2° C. and 10° C., preferably 2° C. to 5° C., for a first time period, and b.) immersing the tissue in a cold fixation dehydrating agent, preferably an alcohol such as e.g. ethanol, especially 95% ethanol, for a second time period (immediately following the first time period).

Thereby, steps a) and b) are preferably carried out in a sequence. Hence, step a) is preferably immediately (i.e. without any other steps in between) followed by step b).

The immersion in cold fixation dehydrating agent according to step b) of the method is preferably carried out at a temperature between 2° C. and 10° C., preferably 2° C. to 5° C. In particular, the cold fixation dehydrating agent is preferably provided at a temperature between 2° C. and 5° C.

The first time period preferably lies between 2 hours and 35 hours. More preferably, the first time period lies between 18 and 30 hours. Even more preferably, the first time period lies between 24 and 30 hours. The second time period preferably lies between 1 and 48 hours.

The 95% Ethanol or other dehydrating agent, preferably an alcohol, is brought in contact with the sample for a time sufficient for complete impregnation of the tissue specimen.

It has been observed that while immersion in Formalin at room temperature for several hours, as usually recommended and practiced, see Goldstein et al., 2003: Goldstein et al., 2007, results in optimal morphological and antigenic preservation, but poor preservation and fragmentation of RNA, fixation in cold (1° C.-5° C.) Formalin for a time ranging between 18 and 30 hours, followed by immersion in cold 95% Ethanol for a time ranging between 2 and 4 hours, at 2° C.-5° C., sufficient for complete penetration into the tissue specimen, resulted in an optimal preservation not only of the morphological (histological) and antigenic properties, but of the RNA sequences as well.

Hence, with the method according to the invention a satisfactory preservation of mRNA sequences is reached. In particular, sequences preferably longer than 350 nucleotides are obtainable, in order to use the so processed material for gene expression analysis.

This two-step cold formalin fixation process is particular advantageous, since according to the prior known methods only shorter sequences can be obtained out of FFPE tissues, which are unsuitable for proper gene expression analyses.

In a preferred embodiment, prior to the cold treatment in 95% Ethanol of the tissue, excessive Formalin is washed with a rinsing liquid, preferably a saline solution.

The Formalin may be pre-cooled prior to the immersion of the tissue.

Following step b.), the tissue may be dehydrated in one or more alcohols. Furthermore, the tissue may be cleared, impregnated in paraffin wax and then embedded.

In a second aspect, the invention also relates to the use of a non-frozen organic tissue sample, fixed with Formalin using a method as explained above, for gene expression profiling.

The invention also relates to the use of a non-frozen organic tissue sample, fixed with Formalin using a method as explained above for DNA or RNA isolation, such as e.g. mRNA isolation.

In a further aspect, the invention relates to an automated tissue fixation system for fixating organic tissue samples in Formalin, the system being provided with
- a processing cavity, into which organic tissue samples can be inserted,
- at least one cooling unit for providing liquid such as Formalin and/or Ethanol to the processing cavity, wherein the cooling unit is designed to provide liquid at a temperature between 2° C. and 10° C., and
- a control unit for transferring the cooled liquid to the processing cavity.

Thereby, the cooling unit is preferably connected to both a Formalin supply and an Ethanol supply. Moreover, switching means are preferably connected to the cooling unit in order to enable a selective provision of Formalin or ethanol to the cooling unit and hence, to the processing unit.

The cooled alcohol (or alcohol mix), preferably is 95% Ethanol.

Instead of said one cooling unit, two cooling units may be provided, each being designed to provide cooled liquid such as cooled Formalin or Ethanol to the processing cavity. Thereby, the cooling units are preferably designed for being controlled independently from each other. Hence, each cooling unit may be set to a different temperature, e.g. by means of the control unit and/or a designated user interface. Moreover, different temperature curves may be applied to the particular liquid provided to the cooling unit.

According to the invention, the above outlined method may be carried out automatically. This is in particular advantageous, since carrying out the above outlined passages in cold conditions manually in Pathology laboratories is rather cumbersome and time consuming.

The system may furthermore comprise a rinsing liquid reservoir, wherein the control unit is designed to cause tissue in the processing cavity and immersed in said cooled Formalin to be washed with the rinsing liquid and cold Ethanol prior to a further process step such as e.g. dehydration, clearing, paraffin impregnation and/or an embedding process.

The system may furthermore comprise a user interface for setting and optionally graphically displaying a cavity temperature/time profile and/or stirring protocols. Moreover, the user interface may be designed for setting and optionally graphically displaying a dedicated reagents management.

In a further aspect, the present invention relates to an integrated automated tissue processing system being designed for carrying out a method for cold fixation of bio-specimens as outlined above, the system being further designed to carry out a resistance and/or microwave heating of the bio-specimens, followed by processing protocols such as dehydration, clearing and/or paraffin impregnation.

BRIEF DESCRIPTION OF THE DRAWINGS

Further advantages, objects and features of the invention will become evident to the skilled person when going through the following detailed description of preferred embodiments of the invention, when taken in conjunction with the figures of the enclosed drawings.

FIG. 3 shows a perspective sectional side view of an automated histoprocessing system ("histoprocessor"), in particular an automated two-step cold formalin tissue processor system according to the invention.

DETAILED DESCRIPTION OF EMBODIMENTS

Figure 1D:
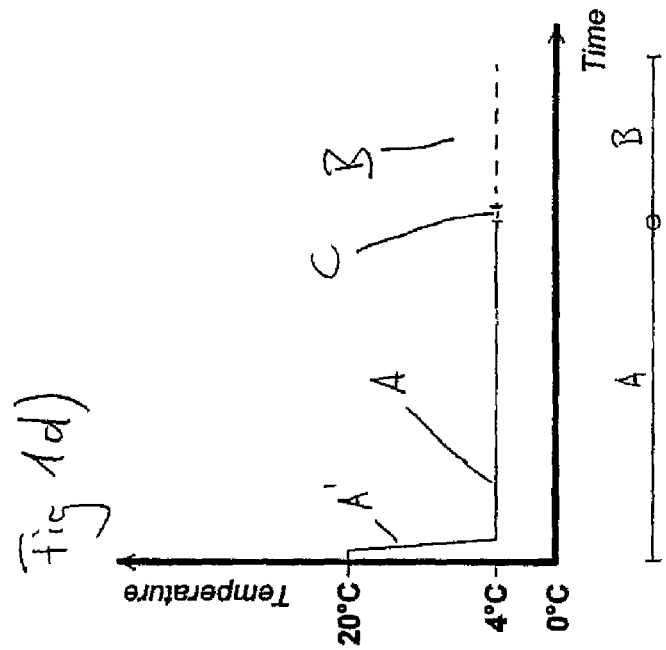
FIG. 1d shows a temperature/time profile illustration the inventive sequential two-step cold formalin fixation according to the invention.
Figure 1A:
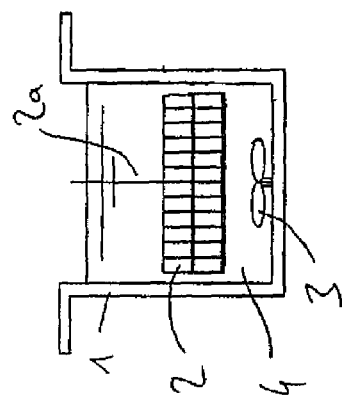
FIG. 1a to 1c show a sectional side view of a processing cavity at different steps of the two-step cold formalin fixation according to the invention.
Figure 1B:
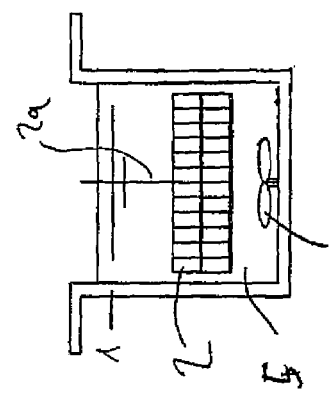
Figure 1C:
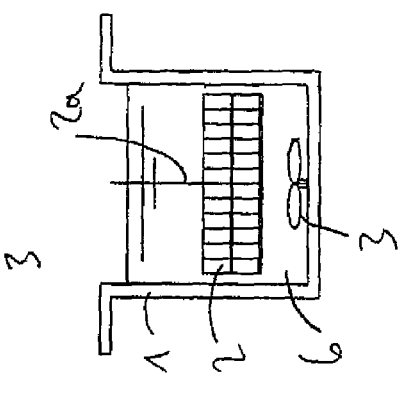

FIG. 1a to 1c relate to a sectional side view of a processing cavity 1 at different steps of the two-step cold formalin fixation according to the invention.

To the processing cavity 1, a sample of biospecimens 2 is provided. Thereby, the sample of biospecimens 2 is preferably held by a rack at a position within the cavity 1 by means of a provided support 2a. The support 2a is preferably designed to enable a positioning of the rack 2 with respect to a stirring mechanism 3 provided within the cavity 1.

As shown in FIG. 1a, a formalin solution 4 is provided to the cavity 1. Thereby, the formalin solution 4 may be provided before or after the provision of the sample of biospecimens 2 to the cavity 1. The formalin solution 4 is preferably of a temperature between 2° C. and 10° C. More preferably, the formalin solution 4 is of a temperature between 2 and 5° C.

The formalin solution 4 is preferably a solution containing 2 to 10% formalin.

A predefined amount of formalin solution 4 is provided in order to fully immerse the provided sample of biospecimens 2.

In a preferred embodiment, the cavity 1 comprises a stirring mechanism 3 arranged at a bottom portion of the cavity 1. The stirring mechanism 3 may be selectively activated for different process steps of the method according to the invention.

During the provision of formalin solution 4 to the cavity 1, the stirring mechanism 3 is preferably activated. Hence a uniform temperature distribution within the cavity 1 respectively of the formalin solution 4 may be obtained.

Figure 2:
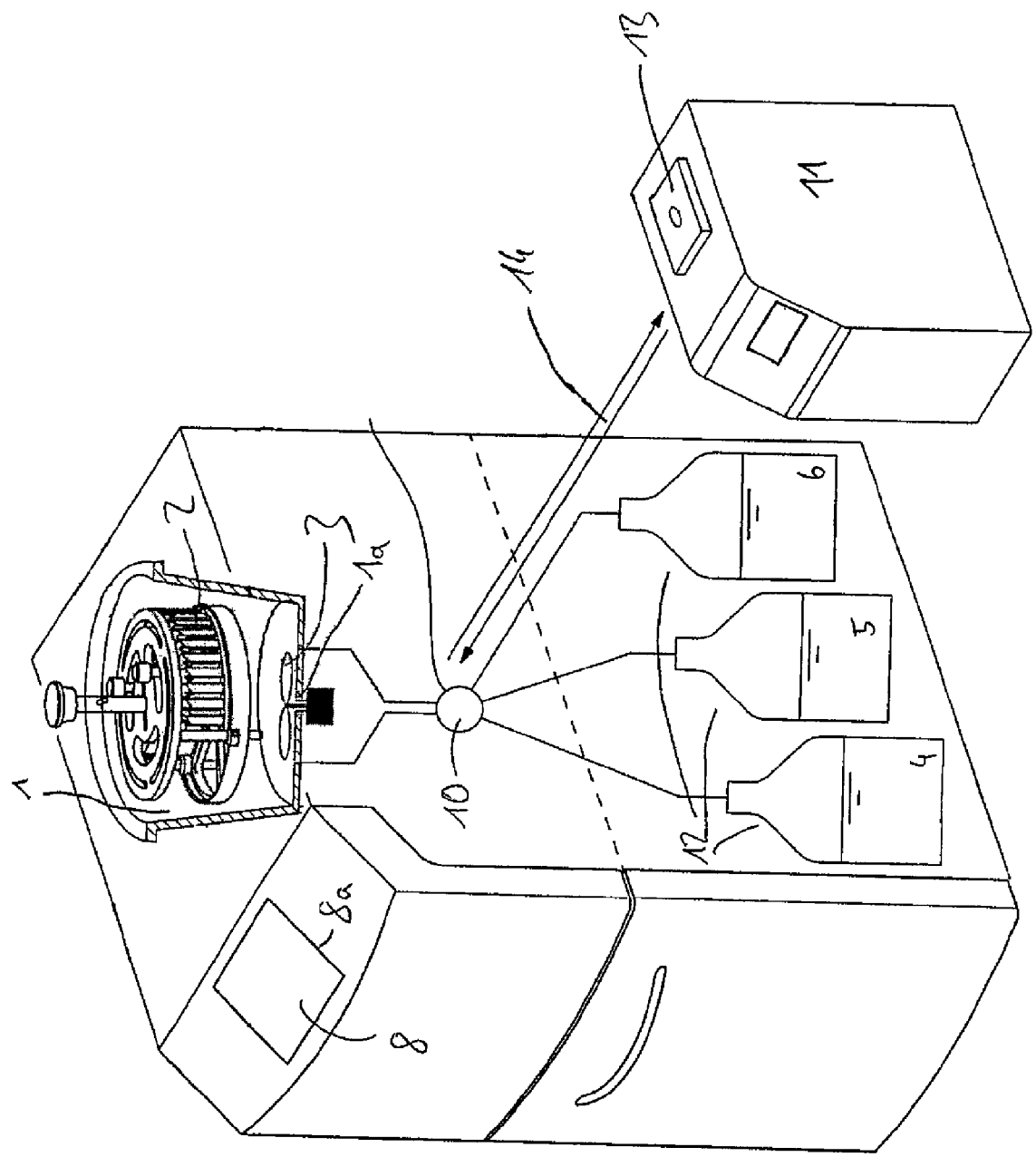
FIG. 2 shows a perspective sectional side view of a two-step cold formalin fixation system for carrying out a two-step cold formalin fixation according to the invention.

The formalin solution 4 is preferably continuously provided to the cavity 1 by means of a dedicated supply system which is to be explained further in the description with reference to FIGS. 2 and 3. Thereby, the level of liquid solution 4 within the cavity 1 is preferably kept constant. Accordingly, the sample of biospecimens 2 is kept fully immersed during the process step.

The formalin solution 4 is preferably provided to the cavity 1 for a predefined first period of time A as indicated in the temperature chart in FIG. 1d. Preferably, the formalin solution 4 is provided for a time period A of 2 to 35 hours. More preferably, the formalin solution 4 is provided to the cavity for a period of time A between 24 hours and 30 hours.

After immersing the sample of biospecimens 2 in formalin solution, the formalin solution is preferably discharged from the cavity 1. Then, in a next step, a flushing respectively a rinsing solution 5 is preferably provided to the cavity 1.

The rinsing solution 5 is preferably a physiological buffered saline solution (PBS). However, any other solution suitable for eliminating excess of formalin traces from the provided sample 2 may be provided to the cavity 1.

The rinsing solution 5 is preferably of a temperature between 2° C. and 10° C., more preferably of a temperature between 2 and 5° C.

The rinsing of the cavity 1 and the sample 2 is preferably carried out for a predefined time C as indicated in FIG. 1d. The rinsing time C is preferably between 1 and 5 minutes.

During the rinsing step, the stirring mechanism is preferably deactivated. However, the stirring mechanism may as well be activated during the rinsing step. Thereby, the stirring mechanism may be rotated at a higher number of revolutions in order to support an effective rinsing of the cavity 1.

In a following step as shown in FIG. 1c, a solution of dehydration respectively fixation agent 6 is provided to the cavity 1 in which the sample of biospecimens 2 is positioned.

The provided agent 6 is preferably an ethanol solution containing between 90 and 97% of ethanol. More preferably, a 95% solution of ethanol is provided to the cavity 1.

Thereby, the ethanol 6 is of a temperature between 2° C. and 10° C. More preferably, the temperature of the ethanol lies between 2 and 5° C.

The ethanol 6 is provided to the cavity 1 for a predefined second time period B as indicated in FIG. 1d. Thereby, the second time period B preferably lies between 1 and 48 hours.

The stirring mechanism 3 is preferably activated during the time period B. Thereby, the number of revolutions of the stirring mechanism 3 may be adapted to differ from the amount of revolutions applied for the first process step relating to immersing the sample 2 in formalin during the time period A.

Moreover, the stirring mechanism 3 may be designed to follow a predefined curve respectively pattern regarding its number of revolutions during a particular process step of the inventive method. Hence, a predefined setup of the number of revolutions of the stirring mechanism 3 may be provided during the process steps of the method. Furthermore, the number of revolutions of the stirring mechanism may be chosen to be dependent on the viscosity of the liquid provided to cavity 1.

It is to be understood that the temperature of the provided liquid such as the provided formalin 4 and the provided ethanol solution 6 is preferably kept at a constant temperature during the fixation process.

Moreover, the provided liquid 4,5,6 is preferably cooled down from room or ambient temperature to a temperature which preferably lies between 2° C. and 10° C. as indicated by curve A' in FIG. 1d.

As shown in FIG. 1d, the temperature is preferably kept constant within the preferred temperature range between 2° C. and 10° C. during the whole process. However, the preferred temperatures of the provided liquid may vary for each process step respectively for each different liquid 4,5,6 provided to cavity 1.

After the provision of ethanol solution 6 to the cavity, the temperature within the cavity 1 may be gradually increased to room temperature.

According to the method of the invention tissue samples 2 are fixed in Formalin which still preserve a good integrity of DNA and mRNA, so that molecular biology procedure can be employed on such material (FFPE tissues) and the gene expression profiling can be adopted on these tissues 2 by sequencing or amplifying mRNA sequences longer than 300 nucleotides.

This inventive sequence of the two-step cold formalin fixation processing (CFP) thus results in an optimal preservation of both histological features and RNA integrity.

FIG. 2 shows a perspective sectional side view of a system for carrying out a two-step cold formalin fixation process according to the invention.

Thereby, the system comprises a cavity 1 into which the sample of biospecimen 2 can be selectively provided.

The system comprises a control unit 8 which is designed for controlling at least the processing time A,B,C of each process step, the reagents sequence, i.e. the particular reagent respectively liquid 4,5,6 to be provided to the cavity 1 at a process step and the particular temperature of the reagent 4,5,6 during the process step.

The control unit 8 is preferably connected at least to a switching valve 10, a cooling unit 11, the stirring mechanism 3, and a pump (not shown) connected to the liquid respectively reagent containers 12. Moreover, temperature sensing means (not shown) optionally arranged within the cavity 1 may be connected to the control unit 8.

Thereby, in order to control the temperature in the cavity 2, there may be at least one (preferably contactless) temperature sensor for detecting the temperature of the wall of the cavity 1 and/or directly or indirectly (infrared etc.) the temperature inside the cavity. The temperature sensor is preferably functionally connected to the control unit 8.

The control unit 8 is preferably equipped with a user interface 8a designed for setting and optionally graphically displaying a cavity temperature/time profile and/or stirring protocols. Accordingly, a user is enabled to set a particular temperature/time protocol for the different processing steps. Moreover, a particular operation profile for the stirring mechanism and/or the supply of liquid to the cavity 1 may be predefined.

The system comprises supply means 10, 12, 1a which enable the selective provision of reagents 4,5,6 to the cavity 1 respectively a discharging of the reagents 4,5,6 therefrom.

In particular, the reagents 4,5,6 are stored in dedicated containers 12 that are each connected to a switching valve 10. The switching valve 10 is connected to the cooling unit 11 of the system that comprises at least one reservoir 13 being designed as a continuous flow cooling unit. Moreover, the switching valve 10 is connected to a supply 1a of the cavity 1 which is preferably formed in the bottom portion of the cavity 1. Accordingly, the supply 1a may be used as combined inlet and outlet for the reagents 4,5,6 to and from the cavity 1.

During a first step a), a solution containing preferably 2 to 10% percentage of formalin is provided to the cavity 1 by means of the supply means 10,12,1a. In particular, the valve 10 is switched to provide formalin solution from the dedicated container 12 to the cooling unit 11 by means of a pump (not shown) connected to each of the container 12. Thereby, the liquid is chilled to a predefined temperature as set by the control unit 8 for the particular process step. The solution then is provided to the cavity 1 by means of the inlet 1a.

In a preferred embodiment, a continuous flow of liquid 14 between the switching valve respectively the cavity 1 and the reservoir 13 of the cooling unit 11 is established, e.g. by a dedicated pump system (not shown). Hence, by means of the continuous flow of liquid, a constant temperature of liquid is obtained.

Thereby, the flow of liquid is preferably chosen such that a constant liquid level is provided within the cavity 1 in order to keep the samples 2 immersed.

During the provision of liquid to the cavity 1, the liquid is agitated by the provided stirring mechanism 3 for homogeneity of temperature and mechanical action for a predefined time period as already explained with reference to FIGS. 1a to 1d.

After the predefined time period, the liquid is then drained back into the dedicated container 12. Thereby, the liquid is discharged through inlet 1a from the container 1 to the respective container 12.

After the provision of formalin solution 4 in step a) of the method according to the invention, the switching valve 10 switches and thus connects the dedicated container 12 of the rinsing solution 5 to the cavity 1 for eliminating excess formalin. After a predefined rinsing time, the rinsing solution 5 is drained back to the dedicated container 12.

In the following step b) of the method according to the invention, the switching valve 10 connects the container storing the ethanol solution 6 which is then provided to the cooling unit 11 and hence, to the cavity 1 for a predefined period of time before it is drained back to the dedicated container.

The pump of the system is preferably integrated within the cooling unit 11 of the system.

Although not depicted in FIG. 2, the cavity 1 is preferably selectively closable by a lid member as for example shown in FIG. 3.

FIG. 3 shows a preferred embodiment of a semi-automatic/automatic two-step cold formalin tissue processor system according to the invention. The system comprises a cavity 1 having a top loading opening selectively closable by lid 15 through which organic tissue samples e.g. on a sample rack 2 can be inserted from above into a cavity 1 of the system.

The cavity 1 is connected to a cooling unit 11 and supply means 10, 12, 1a (see FIG. 2).

Integrated into the system, or at least in fluid connection with the cavity 1 there are several fluid reservoirs 12, i.e. fluid reservoirs at least for:
- formalin,
- PBS solution,
- an alcohol such as ethanol or isopropanol, and
- molten paraffin.

In a first process step according to this embodiment, the tissue samples 2 provided to the cavity 1 are first fixed by the cold fixation process in a preferably automatic sequence as described previously with respect to FIGS. 1 and 2. Thereby, the control unit 8 of the system controls the active transfer of the above listed media into the cavity 2 and out of the cavity.

In a second step, the cavity 1 is filled with ethanol at temperature of 35 to 70° C. for rapid dehydration. The ethanol is preferably heated by dedicated heating means connected to the provided storage container 12 of the ethanol, e.g. a continuous flow heater. Alternatively, a resistance or microwave heating means may be arranged within the cavity 1 of the system. The heating means 17 are preferably connected to the control unit 8 of the system.

The ethanol is then drained from the cavity 1 back to a provided additional container 12.

In a following step, the cavity is filled with a clearing agent such as for example isopropanol, xylene or other suitable solvents for lipids. Thereby, the temperature of the provided solvent is held at a temperature between 35 and 70° C., e.g. by the provided heating means arranged within the cavity 1.

After an evaporation step with or without vacuum, the biospecimens 2 are infiltrated with molten paraffin at a temperature between 65 and 70° C. Thereby, the paraffin may be directly transferred to the cavity 1 by means of dedicated supply piping of the system.

Alternatively, the sample of biospecimens 2 may be provided to an additionally provided cavity 16 of the system to which the paraffin wax may be selectively provided.

The rational basis of the process according to the invention is as follows:

Tissue fixation by formaldehyde, i.e. formation of cross-links, is known to be a slow process, requiring several hours to be completed (Hewitt). Fixation is preceded by the rather fast penetration of the reagent through cell membranes, deep into the tissues at a speed of approximately 1 mm per hour Hewitt, 2008).

It is thought that during the fast phase of penetration through cell membranes, which precedes the slow crosslinking fixation process, fragmentation and degradation of nucleic acids, and especially of RNA, might take place. In fact, membrane disruption would lead to liberation of tissue RNAses and in the lengthy time interval before completion of protein fixation (involving inhibition of enzyme activity) RNAses would be actively engaged in producing the observed RNA fragmentation. In fact, it is known the RNAses are not inhibited by formaldehyde (Ding).

Based on this hypothesis, it has further been considered that RNAse activity would be inhibited by low temperature (Burka). Therefore, in an example of the invention, tissue penetration by formalin is first conducted at 4° C. In sequence, and taking advantage of the fact that tissues are already fixed in cold formaldehyde, the completion of fixation is done by immersing in cold ethanol.

The rational of this passage is based on the fact that Ethanol is a good fixative by coagulation; in addition, it precipitates RNA and inhibits RNAses. If, after the first passage, tissues were transferred in Ethanol at room temperature, and since this dehydration process takes a few hours (2-6) to be completed, during this time tissues would still be exposed to active RNAses. Hence, there is the need to dehydrate in cold condition. Afterwards, processing and paraffin embedding immediately follow.

EXAMPLE

Sample Collection Procedures

Ten tissue specimens, 4 colon cancers and 4 breast carcinomas, one pancreatic and one gastric cancers were obtained.

Immediately after removal, surgical specimens were transferred to the pathology lab and processed without delays. From each specimen three samples were taken and processed as follows:
a) Routine fixation procedure: the sample was 24 h in 4% neutral buffered formalin (NBF) (Histo-Line Laboratories, Milan, Italy) at room temperature (RT), routinely processed and embedded in paraffin wax;
b) Fixation procedure according to the invention (Cold Formalin Processing, CFP): the sample was immersed in pre-cooled 4% NBF (Histo-Line Laboratories, Milan, Italy) at 4° C. from 4 up to 24 hours; then transferred, in pre-cooled 95% Ethanol for 2-6 hours. Then, the specimen were routinely processed by further dehydration in alcohol, clearing, impregnation in paraffin and embedding.
c) Freezing procedure: the sample was frozen in liquid nitrogen immediately after dissection and stored at −80° C.

Staining, Immunohistochemistry and FISH Procedures

Formalin-fixed, paraffin-embedded (FFPE) sections, 3 µm-thick, were routinely stained with hematoxylin and eosin (H&E). Immunohistochemistry was performed on tissue sections using an automated slide processing platform (Ventana BenchMark AutoStainer, Ventana Medical Systems, Tucson, Ariz., USA) and the following primary antibodies:
  CK20 monoclonal mouse antibody (clone Ks 20.8, diluted 1:100, DAKO, Glostrup, Denmark) to stain colon carcinomas;

prediluted anti-ER rabbit monoclonal antibody (clone SP1, Ventana-Diapath, Tucson, Ariz., USA),
prediluted anti-PgR rabbit monoclonal antibody (clone 1E2, Ventana-Diapath),
anti-Ki67 monoclonal antibody (clone MIB1, diluted 1:100 Dako, Glostrup, Denmark), and
anti-HER2 polyclonal antibody (A0485, diluted 1:800, Dako) for breast cancer specimens.

In order to evaluate HER2 gene amplification, FISH (fluorescence in situ hybridization) assays were performed on those cases initially diagnosed as equivocal (score 2+) by immunohistochemistry, as previously reported (Marchiò C. J. Pathol. 2009; 219(1):16-2.). Positive and negative controls (omission of the primary antibody and IgG-matched serum) were included for each immunohistochemical run.

RNA Extraction

RNA was extracted from FFPE and fresh frozen blocks. For each sample, five sections for FFPE specimens (10 μm thick) or ten (or more) sections (20 μm thick) for the frozen ones, were serial sectioned and collected in a 1.5 ml sterile Eppendorf tube. RNA isolation from FFPE samples was performed using the MasterPure Purification kit (Epicentre, Madison, Wis., USA). Sections were deparaffinized by incubations in xylene, followed by incubations with 100% ethanol. Ethanol was discarded and the pellet was air-dried for few minutes at room temperature before Proteinase K treatment, according to Chen optimized extraction "Method 3" for FFPE tissues (Diagn Mol Pathol. 2007; 16(2):61-72.).

RNA extraction from fresh frozen sections was performed with 1 ml of Trizol® reagent (Invitrogen, Carlsbad, Calif., USA), according to manufacturers' instructions. RNA pellets were resuspended in DEPC-treated water and RNA concentration was assessed with a spectrophotometer (BioPhotomer Eppendorf AG, Hamburg, Germany). RNA samples were stored at −80° C. until further analysis.

The quality and quantity of the extracted RNA was also assessed using a Bioanalyzer 2100 (Agilent Technologies, Palo Alto, Calif.) based on a 28S/18S ribosomal RNA ratio and on the "RNA integrity number" (RIN).

DNA Extraction

DNA was isolated from FFPE and fresh frozen blocks. For each sample, five sections for FFPE specimens (10-mm-thick) or ten sections (20-mm-thick) for the frozen ones, were serial sectioned and collected in a 1.5 ml sterile Eppendorf tube. Samples were treated according to the manufacturer's protocol for the QIAamp DNA minikit (QIAGEN Ltd, Crawley, UK). The DNA concentration was measured spectrophotometrically and the eluted DNA was stored at 4° C. until further analysis.

Reverse Transcriptase-Polymerase Chain Reaction (RT-PCR) and PCR Analysis

RT-PCR was performed after a DNAse treatment step with TURBO DNA-free™ Kit (Ambion, Foster City, Calif., USA). For each sample up to 4 μg of RNA were reverse transcribed to cDNA with High-Capacity cDNA Reverse Transcription Kit (Applied Biosystems, Foster City, Calif., USA). RNA samples without Reverse Transcriptase were reverse transcribed as negative controls of DNA contamination for PCR analyses. A multiplex PCR for co-amplification of sequences from Abelson kinase (ABL; ABL1, NM_005157.3, NM_007313.2), porphobilinogen deaminase/hydroxymethylbilane synthase (PBGD; HMBS, NM_001024382.1, NM_000190.3), and beta2-microglobulin (B2M; NM_004048.2) was performed for each sample to prove RNA quality and integrity and to assess the absence of DNA polymerase inhibitors. The ABL/PBGD/B2M genes were amplified using published primers and conditions (Leukemia. 1998; 12:1984-6; discussion 1987-93.). cDNAs from colon cancer samples were subsequently amplified for Cytokeratin 20 (CK-20; KRT20, NM_019010.1) target sequences (329 nt and 500 nt), whereas cDNA from breast cancer specimens were tested for mammaglobin (SCGB2A2, NM_002411.2; 331 nt) (Cancer Res. 1998; 58(20):4581-4) and ER alpha (ESR1, NM_000125.3, NM_001122740.1, NM_001122741.1, NM_001122742.1; 346 nt) gene expression. Each PCR reaction was carried out using POLYTAQ Taq DNA Polymerase (1.5 U final) (Polymed, Florence, Italy). Primers sequences, size of the amplicons and the annealing temperatures are reported in Table 1.

CK-20 (KRT20, NT_010783.15) expression was also evaluated on genomic DNA samples (339 nt, 420 nt, 755 nt). PCR conditions are reported in Table X. Reactions were performed on PTC-100 Peltier Thermal Cycler (MJ Research, Inc., MA, USA). PCR products were separated by electrophoresis on ethidium bromide-stained 2% agarose gel. To reduce the risk of contamination from previously amplified products, separate areas were used for RNA isolation, amplification and electrophoresis.

TABLE 1

PCR conditions

| Target | Gene | Primer sequences | Size | AT |
|---|---|---|---|---|
| cDNA | CK20 | FW1 5'-AGTTCTGCAGCAACAGGTCACAG-'3 | 329 nt | 63.0° C. |
| | | REV 5'-CTTCCAGAAGGCGGCGGTAAGTAG-'3 | | |
| | | FW2 5'-GGAGGAAGTCGATGGCCTACACAA-'3 | 500 nt | |
| | Mammaglobin | FW 5'-AGCACTGCTACGCAGGCTCT-'3 | 331 nt | 58.0° C. |
| | | REV 5'-ATAAGAAAGAGAAGGTGTGG-'3 | | |
| | ER alpha | FW 5'-CTGCTGGCTACATCATCTCG-'3 | 346 nt | 54.0° C. |
| | | REV 5'-TCTCCAGCAGCAGGTCATAG-'3 | | |
| Generade DNA | CK20 | FW 5'-ATGACCCAAGTTCCAGGGGTGACT-'3 | | 66.0° C. |
| | CK20 | REV1 5'-GGTCTGGTCACATGTGGTGTGATG-'3 | 339 nt | |
| | CK20 | REV2 5'-CACAAAGGGCTTTTTGGTGTTAATGC-'3 | 420 nt | |
| | CK20 | REV3 5'-GACAGCAGATGTATGCCACCATGC-'3 | 755 nt | |

Size = Size of PCR product, AT = Annealing temperature.

Results

Specimens (colon cancers and breast cancers) arrived fresh from the surgical theatre were processed in parallel. From each case, one sample was fresh-frozen, one routinely processed for formalin fixation while one or two followed the cold formalin/ethanol fixation process (CFP).

The following aspects have been checked:
1) Morphological (histological) preservation;
2) Immunohistochemical reactivity for routinely used markers, i.e. ER, PgR, Ki67 and HER2 for breast cancer; Ki67, EGFR and CEA for colon cancer;
3) Nucleic acid preservation.

No distinction was observed in morphology and immunoreactivity between tissues processed either routinely or following the CFP procedure, with unaware pathologists occasionally opting for the latter as better. No shrinking or distortion artifacts were observed.

The RNA preservation was initially checked using the RIN procedure. In fresh frozen specimens, serving as control, the value ranged between 8.5 and 7.2. Values were much lower (ranging between 3.6 and 2.3) in RNA samples obtained from paraffin sections of CFP treated tissues.

As expected, the RIN value of RNA samples from routinely processed tissues was not evaluable.

The present study indicates that the poor preservation and fragmentation of nucleic acids, currently observed in formalin fixed tissues can, at least partly be prevented using appropriate temperature conditions. Data of the literature (Dotti et al., 2010; D'Armiento) unanimously indicate that while in alcohol-fixed tissues a successful amplification of relatively long mRNA fragments (in the range of 400-500 bp) can be obtained, only short fragments, up to 200 bp can be amplified out of FFPE tissues. The CFP procedure allowed RT-PCR amplification of DNA fragments and of RNA fragments.

Not unexpectedly, the RNA Integrity Index (RIN) of the RNA extracted for routinely processed tissues was not evaluable. The quality of RNA extracted from CFP processed tissues was poor, though definitely better than routinarily formalin fixed tissues, mainly because of fragmentation of material peaking at 28 S.

Although the RNA quality is often expressed as RIN (rRNA Integrity Index) as evaluated by electrophoresis and Agilent Bioanalyzer, recent evidence has been presented (Dotti et al., 2010) that a more trustful representation of the mRNA integrity is obtained by direct evaluation of tissue specific sequences of different length and end-point RT-PCR.

Evidence of a definite improvement of the preservation of mRNA in CFP processed tissues was assessed by RT-PCR amplification using probes defining different by (base pair) lengths of appropriate markers (CK20 for colon cancer; mammoglobin for breast cancer).

The possibility of obtaining high quality mRNA from FFPE tissues, as permitted by the fixation procedure here presented, opens prospects for gene expression profile analysis wider than those presently feasible (Scicchitano et al., 2006; Abramovitz et al., 2008) and expand the possibility of expression profiling on tissue blocks archived in pathology laboratories.

REFERENCES

1. Blum F. Formaldehyde als Hartungsmittel. *Z wiss Mikr.* 1893; 10:314.
2. Goldstein N S, Hewitt S M, Taylor C R, et al. Recommendations for improved standardization of immunohistochemistry. *Appl Immunohistochem Mol Morphol.* 2007; 15:124-133.
3. Dabbs D J. Immunohistochemical protocols: back to the future. *American journal of clinical pathology.* 2008; 129: 355-356.
4. Goldstein N S, Ferkowicz M, Odish E, et al. Minimum formalin fixation time for consistent estrogen receptor immunohistochemical staining of invasive breast carcinoma. *American journal of clinical pathology.* 2003; 120: 86-92.
5. Wolff A C, Hammond M E, Schwartz J N, et al. American Society of Clinical Oncology/College of American Pathologists guideline recommendations for human epidermal growth factor receptor 2 testing in breast cancer. *J Clin Oncol.* 2007; 25:118-145.
6. Medeiros F, Rigl C T, Anderson G G, et al. Tissue handling for genome-wide expression analysis: a review of the issues, evidence, and opportunities. *Archives of pathology & laboratory medicine.* 2007; 131:1805-1816.
7. Lewis F, Maughan N J, Smith V, et al. Unlocking the archive—gene expression in paraffin-embedded tissue. *The Journal of pathology.* 2001; 195:66-71.
8. Chung J Y, Braunschweig T, Williams R, et al. Factors in tissue handling and processing that impact RNA obtained from formalin-fixed, paraffin-embedded tissue. *J Histochem Cytochem.* 2008; 56:1033-1042.
9. Dotti I, Bonin S, Basili G, et al. Effects of formalin, methacarn, and fineFIX fixatives on RNA preservation. *Diagn Mol Pathol.* 19:112-122.
10. van Maldegem F, de Wit M, Morsink F, et al. Effects of processing delay, formalin fixation, and immunohistochemistry on RNA Recovery From Formalin-fixed Paraffin-embedded Tissue Sections. *Diagn Mol Pathol.* 2008; 17:51-58.
11. Paska C, Bogi K, Szilak L, et al. Effect of formalin, acetone, and RNAlater fixatives on tissue preservation and different size amplicons by real-time PCR from paraffin-embedded tissue. *Diagn Mol Pathol.* 2004; 13:234-240.
12. Masuda N, Ohnishi T, Kawamoto S, et al. Analysis of chemical modification of RNA from formalin-fixed samples and optimization of molecular biology applications for such samples. *Nucleic acids research.* 1999; 27:4436-4443.
13. Helander K G. Kinetic studies of formaldehyde binding in tissue. *Biotech Histochem.* 1994; 69:177-179.
14. Fox C H, Johnson F B, Whiting J, et al. Formaldehyde fixation. *J Histochem Cytochem.* 1985; 33:845-853.
15. Pearse A. *Histochemistry, theoretical and applied.* Edinburgh, London and New York.
16. Stanta G, Schneider C. RNA extracted from paraffin-embedded human tissues is amenable to analysis by PCR amplification. *BioTechniques.* 1991; 11:304, 306, 308.
17. Hewitt S M, Lewis F A, Cao Y, et al. Tissue handling and specimen preparation in surgical pathology: issues concerning the recovery of nucleic acids from formalin-fixed, paraffin-embedded tissue. *Archives of pathology & laboratory medicine.* 2008; 132:1929-1935.
18. Sompuram S R, Vani K, Bogen S A. A molecular model of antigen retrieval using a peptide array. *American journal of clinical pathology.* 2006; 125:91-98.
19. Jones D. The reaction of formaldehyde with unsaturated fatty acids during histological fixation. *The Histochemical journal.* 1969; 1:459-491.
20. Ding J, Ichikawa Y, Ishikawa T, et al. Effect of formalin on extraction of mRNA from a formalin-fixed sample: a basic investigation. *Scandinavian journal of clinical and laboratory investigation.* 2004; 64:229-235.
21. Burka E R. RNase activity in erythroid cell lysates. *The Journal of clinical investigation.* 1969; 48:1724-1732.

22. Chen J, Byrne G E, Jr., Lossos I S. Optimization of RNA extraction from formalin-fixed, paraffin-embedded lymphoid tissues. *Diagn Mol Pathol*. 2007; 16:61-72.
23. Scicchitano M S, Dalmas D A, Bertiaux M A, et al. Preliminary comparison of quantity, quality, and microarray performance of RNA extracted from formalin-fixed, paraffin-embedded, and unfixed frozen tissue samples. *J Histochem Cytochem*. 2006; 54:1229-1237.
24. Abramovitz M, Ordanic-Kodani M, Wang Y, et al. Optimization of RNA extraction from FFPE tissues for expression profiling in the DASL assay. *BioTechniques*. 2008; 44:417-423

What is claimed is:

1. An automated tissue fixation system for fixating organic tissue samples, the system comprising:
    a processing cavity, into which organic tissue samples are insertable;
    at least one continuous flow cooling unit comprising at least one reservoir for providing cooled liquid to the processing cavity, wherein the cooled liquid comprises Formalin, a physiological buffered saline (PBS) solution and Ethanol, wherein each of the Formalin, PBS solution and Ethanol is stored in a separate container;
    a switching valve that is connected to each container, the continuous flow cooling unit and a supply of the reservoir of the continuous flow cooling unit, and wherein the continuous flow cooling unit cools liquid at a temperature of between 2° C. and 10° C.; and
    a control unit for transferring the cooled liquid to the processing cavity.

2. The system according to claim 1, the system being further designed to carry out a resistance and/or microwave heating of the organic tissue samples followed by processing protocols including dehydration, clearing and/or paraffin impregnation.

3. The system according to claim 1, further comprising a rinsing liquid reservoir containing rinsing liquid, wherein the control unit is designed to cause tissue in the processing cavity and immersed in the cooled liquid to be washed with the rinsing liquid prior to dehydration.

4. The system of claim 3, wherein the rinsing liquid reservoir contains a physiological buffered saline solution (PBS).

5. The system according to claim 1, further comprising a user interface designed for setting and optionally graphically displaying a cavity temperature/time profile and/or stirring protocols.

6. The system according to claim 1, wherein the control unit is designed for controlling at least one of a processing time; a sequence of the Formalin, PBS solution and Ethanol; or a temperature of the Formalin, PBS solution and Ethanol.

* * * * *